United States Patent [19]

Meyer et al.

[11] Patent Number: 5,409,694
[45] Date of Patent: Apr. 25, 1995

[54] LIQUID DEODORANT COMPOSITIONS

[75] Inventors: Gerard B. Meyer, Hamilton; Joseph A. Listro, Maineville, both of Ohio

[73] Assignee: Procter & Gamble, Cincinnati, Ohio

[21] Appl. No.: 26,249

[22] Filed: Mar. 4, 1993

Related U.S. Application Data

[63] Continuation of Ser. No. 732,385, Jul. 18, 1991, abandoned.

[51] Int. Cl.⁶ .......................... A61K 7/36; A61K 9/10
[52] U.S. Cl. ........................................ 424/67; 514/938
[58] Field of Search .................................. 424/65, 67

[56] References Cited

U.S. PATENT DOCUMENTS

| | | | |
|---|---|---|---|
| 2,865,859 | 12/1958 | Lubowe | 252/56 |
| 2,942,008 | 6/1960 | Lubowe | 252/364 |
| 4,113,852 | 9/1978 | Kenkare et al. | 424/46 |
| 4,264,586 | 4/1981 | Callingham et al. | 424/68 |
| 4,268,499 | 5/1981 | Keil | 424/68 |
| 4,435,382 | 3/1984 | Shin et al. | 424/66 |
| 4,499,069 | 2/1985 | Krafton | 424/66 |
| 4,559,226 | 12/1985 | Fogel et al. | 424/66 |
| 4,673,570 | 6/1987 | Soldati | 424/66 |
| 4,784,844 | 11/1988 | Thimineur et al. | 424/65 |
| 4,788,001 | 11/1988 | Narula | 252/312 |
| 4,801,447 | 1/1989 | Gum | 424/68 |
| 4,874,547 | 10/1989 | Narula | 252/312 |
| 4,906,454 | 3/1990 | Melanson, Jr. et al. | 424/47 |
| 4,973,473 | 11/1990 | Schneider et al. | 424/63 |

FOREIGN PATENT DOCUMENTS

| | | | |
|---|---|---|---|
| 0200548 | 11/1986 | European Pat. Off. | 424/65 |
| 0216558 | 4/1987 | European Pat. Off. | 424/65 |
| 343843 | 11/1989 | European Pat. Off. | 424/47 |
| WO9118586 | 12/1991 | European Pat. Off. | 424/65 |
| WO9118587 | 12/1991 | European Pat. Off. | 424/65 |
| 59-152318 | 8/1984 | Japan | 424/68 |
| 60-193907 | 10/1985 | Japan | 424/65 |
| 62-289512 | 12/1987 | Japan | 424/65 |
| 1536222 | 12/1978 | United Kingdom | 424/68 |
| 2018590 | 10/1979 | United Kingdom | 424/47 |
| 2155337 | 9/1985 | United Kingdom | 424/59 |

OTHER PUBLICATIONS

U.S. patent application Ser. No. 528,296 (Napolione) filed May 24, 1990 Gels and Stick Formulary, vol. 99, Cosmetics & Toiletries pp. 82 & 83 Nov., 1984.
Manufacturing Chemist, Nov. 1952, p. 472, Rae.
Cosmetics & Toiletries, 1985, vol. 100, pp. 27, 29, 35, 36, 68, 69, 71, 72 and 75.
Sagarin Cosmetics, Science and Technology, 1957, pp. 720 and 730.

Primary Examiner—Dale R. Ore
Attorney, Agent, or Firm—Leonard W. Lewis; John M. Howell; Michael E. Hilton

[57] ABSTRACT

Disclosed are liquid deodorant compositions characterized by the presence of water and zinc phenolsulfonate at a weight ratio of at least about 1:3, most preferably about 3:1; most preferably 3:1; low levels of irritation causing polyhydric alcohols; relatively low monohydric alcohol levels; and the presence of nonionic emulsifiers. Also disclosed is a method for treating or preventing human malodor.

25 Claims, No Drawings

LIQUID DEODORANT COMPOSITIONS

This is a continuation of application Ser. No. 732,385, filed on Jul. 18, 1991 now abandoned.

TECHNICAL FIELD

The present invention relates to liquid deodorant compositions comprising the deodorant active zinc phenolsulfonate. These compositions are particularly suitable for use in pump spray dispensers.

BACKGROUND OF THE INVENTION

Deodorant liquid compositions have become part of many people's personal care and grooming regimen. These compositions may be delivered to the body via a variety of devices such as aerosol sprays, pump sprays, and liquid applicators such as roll-on devices. Such forms of liquid deodorants are described, for example, in U.S. Pat. No. 4,906,454, Melanson et. al., issued Mar. 6, 1990.

The formulation of deodorant products is a delicate balancing of perfume, deodorant active, cosmetic factors and skin irritation factors. The resulting product is often a consumer acceptable product but not an outstanding product in all areas.

Historically, perfumes were used to mask body odors. Today, deodorant compositions not only comprise perfumes, but, also, antimicrobials, herein referred to as deodorant actives. The deodorant actives enhance the ability of the perfumes to mask malodors by destroying the microbes which abide on the skin. The microbes attack sweat gland secretions thus causing the formation of malodorous fatty acids. It is through the combined efforts of the perfume and the actives that deodorants are effective. Unfortunately, this effectiveness is diminished when over the shelf life of a liquid deodorant product the volatile ingredients, such as ethanol, degrade the actives into malodorous subcomponents. Particularly, it has been discovered that a highly preferred deodorant active, zinc phenolsulfonate, degrades into malodorous ethoxyphenols in the presence of monohydric alcohols, e.g., ethanol. Thus the shelf life of liquid deodorants comprising zinc phenolsulfonate and monohydric alcohols is greatly diminished. It is one object of this invention to discover a means for preventing degradation of zinc phenolsulfonate in the presence of monohydric alcohols and thereby provide long lasting odor stability and effective deodorancy in a liquid deodorant composition.

Perceived cosmetics can be important to consumers in a liquid deodorant composition, as can odor stability. Aerosol deodorants have gained wide consumer acceptance due to their excellent cosmetic characteristics.

Aerosol deodorants are typically about 20% to 40% propellant, about 50-70% the volatile monohydric alcohol ethanol, and about 5-10% propylene glycol, a deodorant active and fragrance. Typically, only about 20% to 60% of the sprayable contents actually reach the skin since the liquified hydrocarbon propellant vaporizes as it is sprayed. Many consumers perceive aerosol deodorants as being dryer than conventional pump spray liquid deodorants wherein a very high proportion of the liquid deodorant is delivered to the skin. Deodorant aerosol products usually maintain very good cosmetic acceptance relative to conventional deodorant pump spray products.

Formulating a liquid deodorant composition suitable for application to the skin by a conventional pump spray device and having excellent cosmetics which additionally are comparable to an aerosol-delivered composition is difficult. The use of monohydric alcohols can lead to a cold feel upon application and stinging when applied to an open wound. The use of water can lead to a sticky, wet skin feel. These effects may typically be minimized by the incorporation of emollients, such as volatile and non-volatile silicones, to aid in reducing tackiness and provide a lasting dry feel to the skin. Such emollients, however, can be difficult to formulate into a physically stable liquid deodorant composition. It is a second objective of this invention to provide a liquid deodorant composition suitable for pump spray application which can provide excellent cosmetics which additionally are comparable to those of an aerosol deodorant, and which can exhibit excellent physical product stability.

While balancing the formulation of a liquid deodorant composition to achieve good overall cosmetics and excellent odor stability, one must consider the degree of skin irritation which will be caused by application of the composition to the skin general, many people find the volatile carrier ingredients, e.g., ethanol, to be irritating to the skin especially when applied to an open wound. It is known in the art that surfactant systems are generally harsh to the skin. The use in liquid deodorant compositions of certain polyhydric alcohols, such as dipropylene glycol, in combination with polypropylene glycol (PPG) ethers of $C_4$-$C_{22}$ fatty alcohols and acids, such as PPG-3 myristyl ether, were found to be irritating to the skin, i.e., cause redness/rash. It is another objective of this invention to provide a liquid deodorant composition suitable for pump spray application which exhibits low skin irritation.

Generally, in the formulation of liquid deodorants useful for pump spray applications, it has been attempted in the industry to solve each of the problems associated with deodorant active stability, cosmetics and skin irritation. These attempts generally have resulted in an improvement, in one or two areas, at the expense of the others or have otherwise provided limited overall improvement. According to the present invention, long lasting odor stability, excellent cosmetics comparable to aerosols, and low skin irritation can be achieved in a stable liquid deodorant composition suitable for delivery in a pump spray device. Furthermore, the deodorant compositions of the present invention still can provide excellent realodor control and overall deodorant performance.

SUMMARY OF THE INVENTION

According to the present invention, stable, low irritation zinc phenolsulfonate-containing liquid deodorants are provided by incorporating into the compositions water at a water: zinc phenolsulfonate at a weight ratio of at least about 1:3, most preferably at about 3:1. The compositions hereof are further characterized by the combination of low or zero level of irritation-causing polyhydric alcohols, and relatively low monohydric alcohol level, relatively high emollient level, and nonionic emulsifier.

More particularly, the present invention provides a liquid deodorant composition, comprising:
  a) from about 15% to about 50%, by weight, of $C_1$-$C_4$ monohydric alcohol;

b) from about 0.1% to about 4%, by weight, of zinc phenolsulfonate;

c) at least about 0.03%, by weight, water wherein the weight ratio of water to zinc phenolsulfonate is at least about 1:3;

d) from about 10% to about 40%, by weight, of a nonionic emulsifier;

e) from about 20% to about 50%, by weight, of a volatile silicone emollient;

f) from about 0.25% to about 15%, by weight, of a non-volatile silicone emollient;

g) from 0% to about 5%, by weight, of a polyhydric alcohol selected from the group consisting of propylene glycol, dipropylene glycol, polypropylene glycols having three or more propylene monomer units, ethylene glycol, diethylene glycol, hexylene glycol, butylene glycol, and mixtures thereof;

h) perfume; and i) from 0% to about 15%, by weight, of an additional non-volatile emollient.

These deodorant compositions are particularly useful for delivery by non-aerosol, pump spray devices. However, other liquid applicators may be used. This invention also provides methods for treating or preventing perspiration-induced human malodors.

DETAILED DESCRIPTION OF THE INVENTION

The components utilized in the present invention are described in detail below.

All percentages and ratios herein are by weight unless otherwise indicated.

Compositions of the present invention are preferably single phase solutions or emulsions which remain stable over a typical shelf life of said compositions.

Monohydric Alcohols

The $C_1$–$C_4$ monohydric alcohols are used in the liquid deodorant compositions of the present invention as a liquid solvent vehicle.

$C_1$–$C_4$ monohydric alcohols are used in the liquid deodorant compositions of the present invention at levels of from about 15% to about 50%, preferably from about 20% to about 45%. Most preferred is a level of from about 25% to about 35%.

Examples of suitable $C_1$–$C_4$ monohydric alcohols include methanol, ethanol, isopropanol and mixtures thereof. The preferred $C_1$–$C_4$ monohydric alcohol for use in the present compositions is ethanol.

Deodorant Active and Water

The deodorant active zinc phenolsulfonate is used at levels of from about 0.1% to about 4%, preferably from about 0.3% to about 3.5%, of the liquid deodorant compositions of the present invention. Zinc phenolsulfonate is most preferably present in compositions of the present invention at a level of from about 0.5% to about 3%.

As discussed above, zinc phenolsulfonate tends to degrade over time into malodorous ethoxyphenols when in the presence of ethanol. Water is present in the present compositions at a level of at least about 0.03% by weight, preferably at least about 0.3%, such that the weight ratio of water to zinc phenolsulphonate is at least about 1:3, preferably from about 3:1 to about 4:1 and most preferably about 3:1. It has been found that the presence of water in these compositions can inhibit the degradation of the deodorant active. The resulting liquid deodorant compositions can exhibit long lasting odor stability.

Zinc phenolsulfonate is the substituted phenol that conforms generally to the formula:

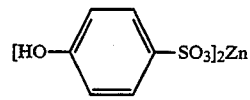

which may be commercially supplied, for example, as octahydrate crystal s or powder.

The maximum amount of water which may be used in particular compositions of the present invention will be determined by the ability to provide the composition in a physically stable form, e.g., as a solution (single phase) or an emulsion. The maximum amount will vary depending upon the selection and level of other components in the composition, and can be easily determined for a particular composition by one of ordinary skill in the art.

Preferably, compositions of the present invention will comprise no more than about 10% water. More preferably, compositions of the present invention will comprise no more than about 5% water.

The levels given for the water component correspond to water in aqueous form, and do not include water that may be added as part of a zinc phenolsulfonate complex.

Nonionic Emulsifier

The compositions of the present invention comprise from about 10% to about 40%, preferably from about 10% to about 30%, and most preferably from about 15% to about 25%, of a nonionic emulsifier.

Nonionic emulsifiers suitable for use in the compositions of the present invention are polypropylene glycol (PPG) ethers of $C_4$–$C_{22}$, preferably $C_{10}$–$C_{20}$, more preferably $C_{12}$–$C_{14}$, fatty alcohols and acids. Also, preferably, these emulsifiers have two to about five, more preferably three to four, propylene glycol units. These emulsifiers can have linear and branched chains, as well as unsaturated chains (e.g. carbon-carbon double bonds).

Examples of emulsifiers include PPG-2 myristyl ether, PPG-4 lauryl ether, PPG-10 cetyl ether, PPG-3 myristyl ether, PPG-11 stearyl ether, PPG-15 stearyl ether, PPG-10 oleyl ether, PPG-3 adipate, PPG-9 laurate and mixtures thereof. Additional examples are found in CTFA Cosmetic Ingredient Dictionary, Third Edition (Extrin et al., Editors; The Cosmetic, Toiletry and Fragrance Association, Inc., 1982), pages 252–260 and 494–500, the disclosures of which are incorporated by reference herein. The most preferred nonionic emulsifier for use in the present compositions is PPG-3 myristyl ether.

Emollients

The present liquid deodorant compositions can comprise relatively large amounts of volatile silicone emollients and non-volatile silicone emollients, and can also comprise additional non-volatile emollients. These emollient components are essential for providing a smooth, non-sticky, dry feel upon application to the skin.

Generally, these emollients are present at a total level of from about 20% to about 80%, preferably from about 25% to about 60% and most preferably from about 35% to about 55%.

The mixture of emollient materials should generally have a viscosity in the range of from about 0.65 centistokes to about 50 centistokes as measured by a Brookfield ® cone and plate viscometer, at 25° C. Generally, the mixture of emollient materials must also be of a certain polarity to remain stable in the present compositions. The precise polarity will depend upon the selection and level of other components of the composition, as will be understood by those skilled in the art. Polarity of the emollients can be characterized in terms of solubility parameter. In general, the solubility parameter (units equal $(ca/cm^3)^{1\ 2}$) should be less than about 10.

The solubility parameter is defined in the *Polymer Handbook* 3rd Ed. (John Wiley and Sons, New York), J Brandrup and E. H. Immergut, Chapter VII, PP. 519–559, as the square root of the cohesive energy density and describes the attractive strength between molecules of the material. The solubility parameters for the present emollient materials can be determined by surface tension measurement as outlined in Vaughan, C. D., *J. Soc. Cosmet. Chem.*, 36, 319–333, 1985. Solubility parameters may also be determined by other measurement procedures, correlations with other physical properties, or indirect measurement which provide equivalent results.

Volatile Silicone Emollient

Volatile silicone emollients for use in the liquid deodorant compositions of the present invention have a viscosity of from about 0.65 centistokes to about 10 centistokes at 25° C.

A description of volatile silicones is found in Todd and Byers, "Volatile Silicone Fluids for Cosmetics", *Cosmetics and Toiletries*, 91:27–32 (1976), incorporated herein by reference. Volatile silicones useful herein are also disclosed in U.S. Pat. No. 4,874,868, Bolich, Jr., issued Oct. 17, 1989, incorporated by reference herein. A preferred volatile silicone for use in the present compositions, which is disclosed in that patent, is phenethyl pentamethyl disiloxane.

By "volatile" silicone, as is well known and understood in the art, is meant that the silicone fluids of which the volatile silicone emollient is comprised are readily vaporizable (i.e., they exhibit an appreciable vapor pressure) at ambient temperatures (particularly at about 20° to 25° C.).

Cyclic volatile siloxanes useful herein include those of the following formula:

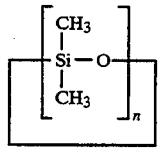

wherein n is from about 3 to about 9.

Linear volatile siloxane oils include those of the formula:

wherein n is from about 1 to about 9. Linear volatile siloxanes generally have viscosities of less than about 5 centistokes at 25° C., and preferably less than about 1 centistoke at 25° C., whereas the cyclic volatile siloxanes generally have viscosities less than about 10 centistokes at 25° C. The most preferred volatile siloxanes for use in the compositions of the present invention are cyclic compounds, i.e., cyclomethicones. The most preferred cyclic siloxanes are those containing about 4 or 5 silicone monomer units, i.e., D4 or D5 cyclomethicones. Examples of the volatile siloxane oils useful in the present invention include Silicone 344 Fluid, Silicone 345 Fluid (sold by Dow Corning Corporation); and Silicone SF-1173 (sold by General Electric Company).

The present liquid deodorant compositions preferably comprise from about 20% to about 50%, preferably from about 25% to about 45%, and most preferably from about 30% to about 40%, of the volatile silicone emollient. Preferred volatile silicone emollients for use in the present compositions are selected from the group consisting of D4 cyclomethicones, D5 cyclomethicones, dimethicone fluids having viscosities of less than about 1 centistoke at 25° C., and mixtures thereof. The most preferred volatile silicone emollients for use herein are cyclomethicones containing about 4 or 5 silicone monomer units, i.e., D4 cyclomethicone, D5 cyclomethicone, and mixtures thereof.

Non-volatile Silicone Emollient

Another essential component of the present invention is a non-volatile silicone emollient. The non-volatile silicone emollient can comprise one or more silicone fluid materials, but should have an "average" viscosity within the range of from about 1 centistoke to about 50 centistokes, preferably from about 10 centistokes to about 20 centistokes, at 25° C. By "average viscosity" is meant that the non-volatile silicone emollient can have one or more non-volatile silicone emollients outside of the specified range of about 1 to about 50 centistokes, but the overall, i.e., the weighted average, viscosity should be within said range. Viscosity can be measured by a Brookfield ® cone and plate viscometer, or other equivalent method. By "non-volatile" silicone, as is well known and understood in the art, is meant that the silicone fluids of which the non-volatile silicone emollient is comprised are not readily vaporizable (i.e., they do not exhibit an appreciable vapor pressure) at ambient temperatures (particularly at about 20° to 25° C.).

The non-volatile silicone emollients that may be used in the present compositions include polyalkyl siloxanes, polyalkylaryl siloxanes, and polyether siloxane copolymers, and mixtures thereof. Preferred non-volatile silicone emollients are linear polyalkyl siloxanes, especially linear polydimethyl siloxanes (i.e., dimethicone). Preferred non-volatile emollients for use have viscosities of from about 10 centistoke to about 20 centistokes at 25° C. These siloxanes are available, for example, from the General Electric Company (Silicone Products Division, Waterford, N.Y., U.S.A.) in the Viscasil TM series and from Dow Corning Corporation (Midland, Mich., U.S.A.), as the Dow Corning 200 Fluid series.

Other non-volatile silicone emollients that can be used include polymethylphenylsiloxanes. These siloxanes are available, for example, from the General Electric Company as SF 1075 methyl phenyl fluid or from Dow Corning as 556 Fluid.

A polyether siloxane copolymer that may be used is, for example, a dimethyl polyoxyalkylene ether copolymer fluid. Such copolymers are available, for example, from the General Electric Company as SF-1066 organosilicone surfactant.

Preferred non-volatile silicone emollients for use are linear polydimethyl siloxanes and phenyl dimethicone.

The present liquid deodorant compositions comprise from about 0.25% to about 15%, preferably from about 0.5% to about 10% and most preferably from about 1% to about 5%. The most preferred non-volatile silicone emollient for use herein is the Dow Corning 200 Fluid series (linear polydimethyl siloxanes).

Additional Non-Volatile Emollient

Additional non-volatile emollients may be incorporated into compositions of the present compositions, but are not required. Non-volatile emollients suitable for use in the liquid deodorant compositions are well known by those of skill in the art. Preferred additional non-volatile emollients include hydrocarbons, mineral oils, fatty alcohols, esters formed by the reaction of $C_3$–$C_8$ fatty alcohols with $C_3$–$C_{18}$ a fatty acids, esters formed by the reaction of benzoic acid and $C_{12}$–$C_{18}$ a alcohols, and mixtures thereof. The preferred additional emollients include, for example, diisopropyl adipate, isopropyl myristate, isopropyl palmitate, $C_{12}$–$C_{15}$ alcohols benzoate, and mixtures thereof. The most preferred additional non-volatile emollients for use are $C_{12}$–$C_{15}$ alcohols benzoate. Other non-volatile emollients include, but are not limited to, glycerine, and polyethylene glycol (PEG) having three or more ethylene monomer units. Such materials include, for example, PEG-3, (i.e. PEG with 3 ethylene monomer units), PEG-4, PEG-6, PEG-8 and mixtures thereof.

The liquid deodorant compositions of the present invention comprise from 0% to about 15%, preferably from about 5% to about 15% and most preferably from about 6% to about 12% of an additional non-volatile emollient. The total level of PEG emollients and glycerine is preferably no more than about 10% more preferably 0% to about 5%. Most preferably, the compositions are essentially free (e.g. 0% to no more than about 1%) of PEG emollient and glycerine.

Polyhydric Alcohols

It has been found that combinations of certain polyhydric alcohols and nonionic emulsifiers, such as PPG-3 myristyl ether, can cause skin irritation (redness/rash) in liquid deodorant compositions.

Accordingly, the compositions of the present invention comprise zero or limited amounts of such irritation-causing alcohols. Specifically, the compositions hereof comprise from 0% to about 5%, preferably less than about 1% and more preferably 0% (i.e. the composition is free of), by weight, of polyhydric alcohols selected from the group consisting of propylene glycol, dipropylene glycol, polypropylene glycols having three or more propylene units, ethylene glycol, diethylene glycol, hexylene glycol, butylene glycol, and mixtures thereof.

Perfume

Perfumes, or fragrances, are generally present in the compositions hereof to mask malodors. Perfumes can also provide a aesthetically pleasing scent to the products. In the present invention, perfume is typically present at a level of at least about 0.1%, preferably from about 0.3% to about 6%, and more preferably from about 1% to about 4%.

Perfumes are made by those skilled in the art in a wide variety of fragrances and strengths. Typical perfumes are described in Arctander, *Perfume and Flavour Chemicals* (Aroma Chemicals), Vol. 1 and II (1969); and Arctander, *Perfume and Flavour Materials of Natural Origin* (1960). The perfumes selected for use herein are chosen not only for their scent and strength, but also to meet the aesthetic demands of the consumer. Perfumes useful in the present invention are any which are suitable for use in the cosmetic industry.

Additional Ingredients

Dyes, pigments, coloring agents and other ingredients known in the art may be included in the compositions hereof for cosmetic or other purposes. Dyes, pigments, and coloring agents typically are used at from about 1 part per million (ppm) to about 10 ppm and are selected from those acceptable for use in drug and cosmetic products.

Method of Manufacture

The processes for making liquid deodorant compositions having long lasting odor stability, excellent cosmetics and low skin irritation, and the equipment used in such processes, are well known to those skilled in the art. Such compositions are batch processed (i.e., discrete processing steps are used).

Liquid deodorants are generally made at room temperature. Depending on the equipment and ingredients, best results may be seen when the zinc phenolsulfonate is dissolved in the ethanol and/or water and the remaining ingredients are added from most polar to least polar. Agitation is required throughout the processing to preferably achieve a homogeneous single phase end product.

Method of Use

The deodorant compositions described herein are utilized in conventional ways to treat or prevent the development of malodors of the human body. Specifically, a safe and effective amount of the liquid deodorant composition is applied topically to the body (e.g., axillary areas) one or more times a day, preferably using a pump spray device although any of the delivery systems for liquid deodorants may also be used. When this is done, malodors are effectively prevented from developing without sacrificing good aesthetics upon application for the user. The compositions of the present invention provide for long lasting odor stability, excellent cosmetics and low skin irritation.

The following non-limiting examples illustrate the compositions and methods of making and using the compositions of the present invention.

EXAMPLE I

A single phase liquid pump spray deodorant composition of the present invention is as follows:

| Component | Weight % |
| --- | --- |
| Ethanol 200 Proof | 30.0 |
| Water | 3.5 |
| PPG-3 Myristyl Ether | 15.0 |
| $C_{12}$—$C_{15}$ Alcohols Benzoate[1] | 9.0 |
| D4 Cyclomethicone[2] | 27.7 |
| D5 Cyclomethicone[3] | 10.0 |
| 10 cS Dimethicone[4] | 1.0 |
| Zinc Phenolsulfonate[5] | 1.0 |
| Perfume | 2.8 |
| | 100% |

[1]Available under the tradename Finsolv TN ® from Finetex, Inc.
[2]Available under the tradename Silicone 344 from Dow Corning.
[3]Available under the tradename Silicone 345 from Dow Corning.
[4]Available under the tradename Silicone 200 Fluid Series from Dow Corning.
[5]Available from Mallinckrodt.

The liquid deodorant compositions of the present invention are made at room temperature using the following method.

Premix the zinc phenolsulfonate with the ethanol and water in a mixing tank, stirring until the zinc phenolsulfonate is dissolved. Add all of the remaining ingredients from the most polar to the least polar. Stir the mixture until a single phase homogeneous product is achieved.

EXAMPLE II

A single phase liquid pump spray deodorant composition of the present invention is as follows:

| Component | Weight % |
| --- | --- |
| Ethanol 200 Proof | 45.0 |
| Water | 1.0 |
| PPG-3 Myristyl Ether | 10.0 |
| $D_4$ Cyclomethicone | 35.0 |
| 20 cs Dimethicone[1] | 7.0 |
| Zinc Phenolsulfonate | 1.0 |
| Perfume | 1.0 |
| | 100% |

[1]Available under the tradename Silicone 200 Fluid Series from Dow Corning.

The composition is made as in Example I.

EXAMPLE III

A single phase liquid pump spray deodorant composition of the present invention is as follows:

| Component | Weight % |
| --- | --- |
| Ethanol 200 Proof | 35.0 |
| Water | 8.0 |
| PPG-3 Myristyl Ether | 25.0 |
| $D_4$ Cyclomethicone | 21.0 |
| $D_5$ Cyclomethicone | 5.0 |
| 5 cS Dimethicone[1] | .5 |
| Zinc Phenolsulfonate | 2.7 |
| Perfume | 2.8 |
| | 100% |

[1]Available under the tradename Fluid 200 Series from Dow Corning.

The composition is made as in Example I.

EXAMPLE IV

A single phase liquid deodorant composition of the present invention, which is suitable for pump spray dispensers, is as follows:

| Component | Weight % |
| --- | --- |
| Ethanol 200 Proof | 5.0 |
| Isopropanol | 30.0 |
| Water | .5 |
| Zinc Phenolsulfonate | 1.0 |
| $D_4$ Cyclomethicone | 38.0 |
| 5cS Dimethicone | 1.0 |
| PPG-4 Lauryl Ether | 20.0 |
| Isopropyl Myristate | 3.0 |
| Perfume | 1.5 |
| | 100% |

The composition is made as in Example I.

EXAMPLE V

A single phase liquid deodorant composition of the present invention, suitable for pump spray dispensers, is as follows:

| Component | Weight % |
| --- | --- |
| Ethanol 200 Proof | 25.0 |
| Water | 1.0 |
| Zinc Phenolsulfonate | 2.7 |
| $D_4$ Cyclomethicone | 40.0 |
| 5cS Dimethicone | 2.0 |
| PPG-3 Myristyl Ether | 20.0 |
| Diisopropyl Adipate | 7.3 |
| Perfume | 2.0 |
| | 100% |

The composition is made as in Example I.

All the above compositions, when applied to the axillary areas, can provide effective deodorant protection, long lasting odor stability, excellent cosmetics which are comparable to aerosol deodorants, and low skin irritation.

What is claimed is:

1. A liquid deodorant composition comprising:
    a) from about 15% to about 50%, by weight, of $C_1$–$C_4$ monohydric alcohol;
    b) from about 0.1% to about 4%, by weight, of zinc phenolsulfonate;
    c) from at least about 0.03%, by weight, water wherein the weight ratio of water to zinc phenolsulfonate is at least about 1:3;
    d) from about 10% to about 40%, by weight, of a nonionic emulsifier selected from the group consisting of polypropylene glycol ethers of $C_4$–$C_{22}$ fatty alcohols and polypropylene glycol ethers of $C_4$–$C_{22}$ fatty acids and mixtures thereof, having from 2 to about 5 propylene glycol units;
    e) from about 20% to about 50%, by weight, of a volatile silicone emollient;
    f) from about 0.25% to about 15%, by weight, of a non-volatile silicone emollient;
    g) from 0% to about 5%, by weight, of polyhydric alcohol selected from the group consisting of propylene glycol, dipropylene glycol, polypropylene glycols having at least three propylene units, ethylene glycol, diethylene glycol, hexylene glycol, butylene glycol, and mixtures thereof;
    h) perfume; and
    i) from 0% to about 15%, by weight, of additional non-volatile emollient.

2. A liquid deodorant composition according to claim 1 wherein the additional non-volatile emollient is selected from the group consisting of hydrocarbons; mineral oils, fatty alcohols, esters formed by the reaction of $C_3$–$C_{18}$ fatty alcohols with $C_3$–$C_{18}$ fatty acids, esters formed by the reaction of benzoic acid and $C_{12}$–$C_{18}$ fatty alcohols, glycerine, polyethylene glycol having at least three ethylene monomer units, and mixtures thereof.

3. A liquid deodorant composition according to claim 2 wherein the combined level of glycerine and polyethylene glycol is no more than about 10% by weight of composition.

4. A liquid deodorant composition according to claim 1 comprising less than about 1% by weight of a polyhydric alcohol selected from the group consisting of propylene glycol, dipropylene glycol, polypropylene glycols having at least three propylene units, ethylene glycol, diethylene glycol, hexylene glycol, butylene glycol, and mixtures thereof.

5. A liquid deodorant composition according to claim 4 wherein the composition is free of polyhydric alcohols.

6. A liquid deodorant composition according to claim 1 wherein the perfume is present from about 0.3% to about 6%, by weight.

7. A liquid deodorant composition according to claim 1 wherein said composition comprises no more than about 10%, by weight, water.

8. A liquid deodorant composition according to claim 1 wherein the $C_1$–$C_4$ monohydric alcohol is selected from the group consisting of methanol, ethanol, isopropanol, and mixtures thereof.

9. A liquid deodorant composition according to claim 8 wherein the $C_1$–$C_4$ monohydric alcohol is present from about 20% to about 45%, by weight.

10. A liquid deodorant composition according to claim 9 wherein the $C_1$–$C_4$ monohydric alcohol is ethanol.

11. A liquid deodorant composition according to claim 7 wherein the weight ratio of water to zinc phenolsulfonate is from about 3:1 to about 4:1.

12. A liquid deodorant composition according to claim 11 wherein the weight ratio of water to zinc phenolsulfonate is about 3:1.

13. A liquid deodorant composition according to claim 1 wherein the emulsifier is PPG-3 myristyl ether.

14. A liquid deodorant composition according to claim 13 wherein the emulsifier is present in the composition at a level of from about 10% to about 30%, by weight.

15. A liquid deodorant composition according to claim 1 wherein the volatile silicone emollient is selected from the group consisting of dimethicone fluids having viscosities of less than about 5 centistoke at 25° C., cyclomethicones, and mixtures thereof.

16. A liquid deodorant composition according to claim 15 wherein the volatile silicone emollient is present in the composition at a level of from about 25% to about 45%, by weight.

17. A liquid deodorant composition according to claim 15 wherein the non-volatile silicone emollient is selected from the group consisting of phenyl dimethicone, linear polydimethylsiloxanes, and mixtures thereof.

18. A liquid deodorant composition according to claim 17 wherein the non-volatile silicone emollient is present in the composition at a level of from about 0.5% to about 10%.

19. A liquid deodorant composition according to claim 1 wherein the additional non-volatile emollient is present in the composition at a level of from about 5% to about 15%, by weight.

20. A liquid deodorant composition according to claim 19 wherein the additional non-volatile emollient is selected from the group consisting of diisopropyl adipate, isopropyl myristate, isopropyl palmitate, $C_{12}$–$C_{15}$ alcohol benzoate, and mixtures thereof.

21. A sprayable, liquid deodorant composition comprising:
   from about 25% to about 35%, by weight, of a $C_1$–$C_4$ monohydric alcohol selected from the group consisting of methanol, ethanol, isopropanol and mixtures thereof;
   b) from about 1% to about 3%, by weight, of zinc phenolsulfonate;
   c) from at least about 0.3% to no more than about 5%, by weight, water wherein the weight ratio of water to zinc phenolsulfonate is at least about 1:3;
   d) from about 15% to about 25%, by weight, of a nonionic emulsifier selected from the group consisting of polypropylene glycol ethers of $C_4$–$C_{22}$ fatty alcohols and polypropylene glycol ethers of $C_4$–$C_{22}$ fatty acids and mixtures thereof, having from 2 to about 5 propylene glycol units;
   e) from about 30% to about 40%, by weight, of a volatile silicone emollient selected from the group consisting of cyclomethicones, and dimethicone fluids having viscosities of less than about 1 centistoke at 25° C., and mixtures thereof;
   f) from about 1% to about 5%, by weight, of a non-volatile silicone emollient selected from the group consisting of phenyl dimethicone, linear polydimethylsiloxanes and mixtures thereof;
   g) perfume
   h) from about 6% to about 12%, by weight, of a non-volatile emollient selected from the group consisting of diisopropyl adipate, isopropyl myristate, isopropyl palmitate, $C_{12}$–$C_{15}$ alcohol benzoate, and mixtures thereof; and
   i) said composition comprising less than 1%, by weight, of polyhydric alcohol selected from the group consisting of propylene glycol, dipropylene glycol, polypropylene glycols having at least three propylene units, ethylene glycol, diethylene glycol, hexylene glycol, butylene glycol, and mixtures thereof.

22. A liquid deodorant composition according to claim 21 wherein the ratio of water to zinc phenolsulfonate is from about 3:1 to about 4:1, by weight.

23. A liquid deodorant composition according to claim 22 wherein the ratio of water to zinc phenolsulfonate is from about 3:1, by weight.

24. A method for treating or preventing malodor in humans comprising application to an axillary area of an effective amount of the liquid deodorant composition according to claim 1.

25. A method for treating or preventing malodors in humans comprising application to an axillary area an effective amount of the liquid deodorant composition according to claim 21.

* * * * *

UNITED STATES PATENT AND TRADEMARK OFFICE
CERTIFICATE OF CORRECTION

PATENT NO. : 5,409,694
DATED : April 25, 1995
INVENTOR(S) : Gerald B. Meyer, et al It is certified that error appears in the above-indentified patent and that said Letters Patent is hereby corrected as shown below:

Column 12, line 3, "from" should read -- a) from--

Attest:

Signed and Sealed this

Seventh Day of January, 1997

BRUCE LEHMAN

*Attesting Officer*   *Commissioner of Patents and Trademarks*